United States Patent [19]

Lee

[11] Patent Number: 4,509,970

[45] Date of Patent: Apr. 9, 1985

[54] SUBSTITUTED PHENYLPHOSPHINYLOXY- AND PHOSPHINYLTHIO-IMINOCARBOXYLATES USEFUL FOR THE CONTROL OF WEEDS

[75] Inventor: Shy-Fuh Lee, Sunnyvale, Calif.

[73] Assignee: Zoecon Corporation, Palo Alto, Calif.

[21] Appl. No.: 331,496

[22] Filed: Dec. 17, 1981

[51] Int. Cl.$^3$ ............................................. A01N 57/00
[52] U.S. Cl. ............................................. 71/86; 71/87; 260/465 D; 260/465 E; 562/426; 562/435; 562/440; 564/271; 564/272; 564/257; 549/505; 549/75; 546/329; 546/330; 546/333; 560/9; 560/21; 560/35

[58] Field of Search ................. 71/86, 108, 115, 87; 260/465 D, 465 E, 455 P; 560/9, 21, 35, 426, 435, 440; 562/426, 435, 440; 564/272, 271, 257; 549/505, 75; 546/329, 330, 333

[56] References Cited

U.S. PATENT DOCUMENTS

| 4,221,581 | 9/1980 | Rohr et al. | 71/108 |
| 4,225,521 | 9/1980 | Sauers | 71/86 |
| 4,233,056 | 11/1980 | Maier | 71/86 |
| 4,304,936 | 12/1981 | Rohr et al. | 71/108 |
| 4,344,789 | 8/1982 | Krass | 71/115 |

*Primary Examiner*—James H. Reamer
*Attorney, Agent, or Firm*—Hana Dolezalova; Jacqueline S. Larson

[57] ABSTRACT

Novel substituted phenylphosphinyloxy- and phenylphosphinylthio-iminocarboxylates, synthesis thereof, intermediates therefor, and the use of said novel compounds for the control of weeds.

12 Claims, No Drawings

SUBSTITUTED PHENYLPHOSPHINYLOXY- AND PHOSPHINYLTHIO-IMINOCARBOXYLATES USEFUL FOR THE CONTROL OF WEEDS

The present invention relates to novel substituted phenylphosphinyloxy- and phenylphosphinylthio-iminocarboxylates, synthesis thereof, intermediates therefor, and the use of said novel compounds for the control of weeds.

More particularly, the novel compounds of the present invention are represented by the following formula (A):

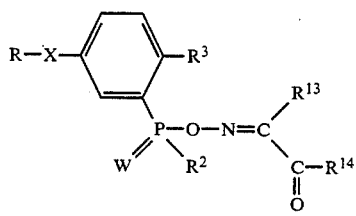

wherein,
R is the group

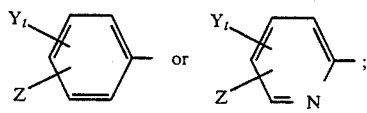

W is oxygen or sulfur;
X is oxygen, sulfur, amino or methylene;
Y is hydrogen, lower alkyl, lower alkoxy, lower haloalkyl, lower haloalkoxy, halogen, cyano or nitro;
Z is independently selected from the values of Y;
t is zero, one or two;
$R^2$ is hydrogen, lower alkyl or phenyl;
$R^3$ is cyano, nitro, nitroso, amino, hydroxyamino or chloro;
$R^{13}$ is hydrogen, lower alkyl, lower cycloalkyl, phenyl, substituted phenyl, furyl or thienyl; and
$R^{14}$ is OH, $O^-Na^+$, lower alkyl, lower alkoxy, lower alkylthio, phenyl, substituted phenyl, phenoxy, phenylthio or benzyloxy.

In the description and claims hereinafter, each of R, $R^2$, $R^3$, $R^{13}$, $R^{14}$, t, W, X, Y and Z is as defined above, unless otherwise specified.

Compounds of the present invention of formula (A) may be synthesized as outlined below (XX=Cl or Br):

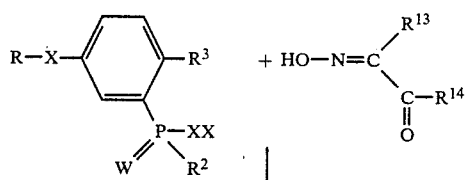

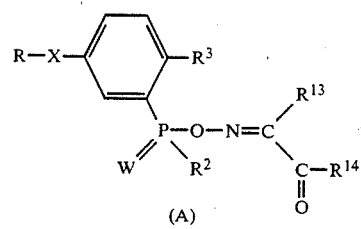

In the above synthesis, a phosphinic chloride (I) is reacted with an oxime (II), most usually at room temperature, in the presence of a solvent such as methylene chloride, tetrahydrofuran or dimethylformamide and with or without a base such as triethylamine or pyridine.

To prepare phosphinic chlorides of formula (I), a phosphinic acid (III) is halogenated by, for example, reaction with a compound such as thionyl chloride or oxalyl chloride at refluxing temperature or below.

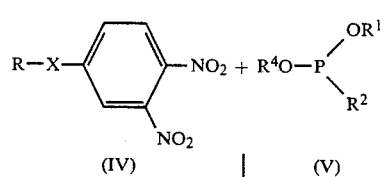

Synthesis of phosphinic acids of formula (III) where $R^3$ is nitro and W is oxygen may be outlined as follows ($R^1$ and $R^4$ each is lower alkyl):

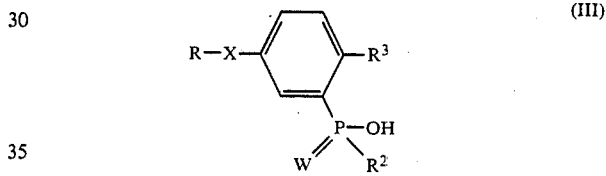

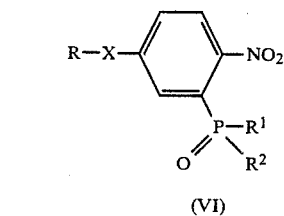

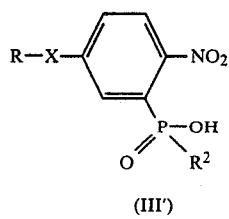

(III')

In the above synthesis, the dinitrobenzene (IV) is phosphinylated with the phosphonite (V) at room temperature or above to give the corresponding phosphinate (VI), following the procedure outlined by Cadogan et al., *J. Chem. Soc.* (C):1314 (1969). The reaction may be carried out neat or in the presence of a solvent such as acetonitrile or tetrahydrofuran. The phosphinate (VI) is then hydrolyzed by reaction with a strong acid such as hydrochloric acid or with trimethylsilyl bromide in methylene chloride or trichloromethane to give the phosphinic acid (III').

The phosphinic acids of formula (III) where $R^3$ is amino can be prepared by the hydrogenation with palladium on carbon under pressure of a phosphinate (VI) ($R^3$=nitro) to the corresponding amino phosphinate, followed by hydrolysis.

To prepare phosphinic acids of formula (III) where $R^3$ is cyano or chloro, a phosphinate corresponding to formula (VI) where $R^3$ is amino is diazotized following the procedure described in *Org. Synth. Coll. Vol.* 1:514 (1932). The diazo salt is then reacted with cuprous cyanide or cuprous chloride to give the corresponding cyano phosphinate (VI where $R^3$=cyano) or chloro phosphinate (VI where $R^3$=chloro), followed by hydrolysis.

Thiophosphinic acids corresponding to formula (III) where W is sulfur can be prepared by reaction of a a phosphinic acid (III where W is oxygen) with, for example, phosphorus pentasulfide at an elevated temperature. In like manner, phosphinothioates corresponding to formula (VI) where W is sulfur can be prepared from a phosphinate (VI) where W is oxygen.

Alternatively, phosphinic chlorides of formula (I) may be synthesized by the reaction of a phosphinate (VI') with thionyl chloride or oxalyl chloride at reflux temperature or below.

To prepare the compounds of formula (A) where $R^3$ is hydroxyamino, a compound of formula (A) where $R^3$ is nitro is reacted with hydrazine, following the procedure described in U.K. patent application 2,035,309, to give the corresponding hydroxyamino compound. Treatment of a hydroxyamino compound of formula (A) ($R^3$=NHOH) with ferric chloride, following the procedure described in U.K. patent application 2,035,309, will give a compound corresponding to formula (A) where $R^3$ is nitroso.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower cycloalkyl" refers to a cycloalkyl group of three to eight cyclic carbon atoms.

The term "substituted phenyl" refers to a phenyl group substituted at one, two or three of the ring carbon atoms with a group selected from lower alkyl, lower haloalkyl, lower alkoxy, lower alkenyl, lower haloalkenyl, lower alkenyloxy, halogen, nitro, cyano or lower alkylthio.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The compounds of the present invention have herbicidal activity on both broad leaf plants and the grassy weeds or graminaceous weeds. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention demonstrate selective activity as herbicides against certain weeds. Crops such as soybean show excellent tolerance.

The following examples are provided to illustrate the practice of the present invention. Temperature is given in degrees Centigrade. "RT" means room temperature.

EXAMPLE 1

A mixture of 4-(2-chloro-4-trifluoromethylphenoxy)-1,2-dinitrobenzene (1.6 g, 4.4 mmol), dimethyl ethylphosphonite (1 ml, 8.8 mmol) and acetonitrile (6 ml) is stirred at room temperature overnight. The reaction mixture is concentrated to dryness, and the residue is purified by preparative thin layer chromatography (silica gel, eluting with 10% ethyl acetate/hexane) to give methyl P-ethyl-2-nitro-5-(2-chloro-4-trifluoromethylphenoxy)phenylphosphinate.

Methyl P-ethyl-2-nitro-5-(2-chloro-4-trifluoromethylphenoxy)phenylphosphinate (1 g) in 20 ml of 6N hydrochloric acid is heated under reflux overnight. The solution is then poured into water and extracted with methylene chloride. The combined solvent extracts are dried over magnesium sulfate and the solvent is then evaporated off to give P-ethyl-2-nitro-5-(2-chloro-4-trifluoromethylphenoxy)phenylphosphinic acid.

A solution of P-ethyl-2-nitro-5-(2-chloro-4-trifluoromethylphenoxy)phenylphosphinic acid (500 mg, 1.22 mmol) and thionyl chloride (4 ml) is heated under reflux for about 1.5 hours. The reaction mixture is then concentrated to dryness to give P-ethyl-2-nitro-5-(2- chloro-4-trifluoromethylphenoxy)phenylphosphinic chloride. To a solution of the phosphinic chloride and methylene chloride (10 ml) is added slowly a solution of ethyl 2-hydroxyiminopropionate (320 mg, 2 eq.) and methylene chloride (5 ml) containing triethylamine (0.2 ml, 1.2 eq.). The resulting mixture is stirred at RT for 2 hours. The reaction is then worked up in methylene chloride, washed, dried and evaporated to dryness to give an oily product. The oily product is purified by preparative thin layer chromatography (prep. TLC) in silica gel (50% ethyl acetate/hexane) to yield ethyl 2-[P-ethyl-2-nitro-5-(2-chloro-4-trifluoromethylphenoxy)phenylphosphinyloxyimino]propionate.

nmr (CDCl₃) δ8.73 (m, 6H, OCH₂CH₃ and PCH₂CH₃), 7.67 (sextet, 2H, PCH₃CH₃), 5.74 (q, 2H, OCH₂CH₃), 1.84–2.97 (m, 6H, aromatic H).

EXAMPLE 2

A mixture of methyl P-ethyl-2-nitro-5-(2-chloro-4-trifluoromethylphenoxy)phenylphosphinate (700 mg, 1.65 mmol) and thionyl chloride (5 ml) is heated under reflux for 2 hours. The reaction mixture is concentrated to dryness to give P-ethyl-2-nitro-5-(2-chloro-4-trifluoromethylphenoxy)phenylphosphinic chloride. To a solution of the phosphinic chloride in methylene chloride (8 ml) is added methyl 2-hydroxyimino-3-methylbutanoate (320 mg, 2.48 mmol) in one portion. The mixture is stirred at RT for 3 hours. The reaction is then worked up in methylene chloride, washed, dried, evaporated to dryness and purified by prep. TLC to yield methyl 2-[P-ethyl-2-nitro-5-(2-chloro-4-trifluoromethylphenoxy)phenylphosphinyloxyimino]-3-methylbutanoate.

nmr (CDCl₃) δ8.97–8.64 (tt, 3H, P—CH₂CH₃), 8.90–8.80 (ss, 6H, —CH(CH₃)₂), 7.44 (m, 3H, P—CH₂CH₃, CH(CH₃)₂), 6.17 (s, 3H, COOCH₃) and 3.00–1.84 (m, 6H, aromatic H).

EXAMPLE 3

Following the procedure of Example 2, P-ethyl-2-nitro-5-(2-chloro-4-trifluoromethylphenoxy)phenylphosphinic chloride is reacted with methyl 2-hydroxyimino-2-phenylacetate (357 mg, 1.5 eq.) in methylene chloride, with stirring at RT for 24 hours. The reaction is worked up and purified as in Example 2 to give methyl 2-[P-ethyl-2-nitro-5-(2-chloro-4-trifluoromethylphenoxy)phenylphosphinyloxyimino]-2-phenylacetate.

nmr (CDCl₃) δ8.97–8.64 (tt, 3H, P—CH₂CH₃), 7.50 (sextet, 2H, P—CH₂CH₃), 6.09 (s, 3H, COOCH₃) and 2.54–1.94 (mm, 11H, aromatic H).

EXAMPLE 4

Following the procedure of Example 2, P-ethyl-2-nitro-5-(2-chloro-4-trifluoromethylphenoxy)phenylphosphinic chloride is reacted with each of the hydroxyimino compounds under column I to prepare the corresponding phosphinyloxyimino compound under column II.

I 1. 3-hydroxyimino-2-butanone
2. 2-hydroxyiminopropanoic acid
3. 2-hydroxyiminopropiophenone
4. 4-hydroxyimino-4-(4-chlorophenyl)-3-butanone
5. 2-hydroxyimino-3-methylbutanoic acid
6. 4′-chloro-2-hydroxyiminobutyrophenone
7. 4-hydroxyimino-3-butanone
8. methyl 2-hydroxyiminoacetate
9. methyl 2-hydroxyiminopropionate
10. n-butyl 2-hydroxyiminopropionate
11. benzyl 2-hydroxyiminopropionate
12. ethyl 2-hydroxyiminopropionthioate
13. phenyl 2-hydroxyiminopropionthioate
14. isobutyl 2-hydroxyiminopropionate
15. phenyl 2-hydroxyiminopropionate

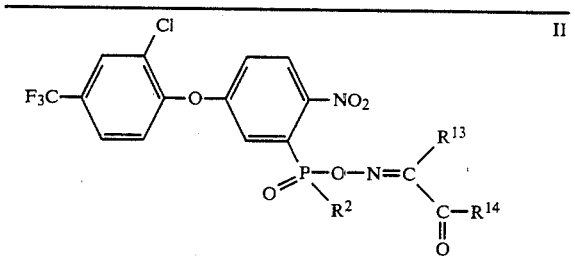

II

| | R² | R¹³ | R¹⁴ |
|---|---|---|---|
| 1. | CH₂CH₃ | CH₃ | CH₃ |
| 2. | CH₂CH₃ | CH₃ | OH |
| 3. | CH₂CH₃ | CH₃ | C₆H₅ |
| 4. | CH₂CH₃ | (4-Cl)C₆H₅ | CH₂CH₃ |
| 5. | CH₂CH₃ | CH(CH₃)₂ | OH |
| 6. | CH₂CH₃ | CH₂CH₃ | (4-CL)C₆H₅ |
| 7. | CH₂CH₃ | H | CH₂CH₃ |
| 8. | CH₂CH₃ | H | OCH₃ |
| 9. | CH₂CH₃ | CH₃ | OCH₃ |
| 10. | CH₂CH₃ | CH₃ | OCH₂CH₂CH₂CH₃ |
| 11. | CH₂CH₃ | CH₃ | OCH₂C₆H₅ |
| 12. | CH₂CH₃ | CH₃ | SCH₂CH₃ |
| 13. | CH₂CH₃ | CH₃ | SC₆H₅ |
| 14. | CH₂CH₃ | CH₃ | OCH₂CH(CH₃)₂ |
| 15. | CH₂CH₃ | CH₃ | OC₆H₅ |

EXAMPLE 5

Following the procedure of Example 1, each of the phosphinic chlorides under column III is prepared from the respective corresponding dinitrobenzene and dimethylphosphonite, followed by hydrolysis and then by halogenation. Each phosphinic chloride is reacted with ethyl 2-hydroxyiminopropionate to give the corresponding phosphinyloxyiminopropionate under column IV.

III

16. P-ethyl-2-nitro-5-(4-trifluoromethylphenoxy)phenylphosphinic chloride
17. P-ethyl-2-nitro-5-(4-chlorophenoxy)phenylphosphinic chloride
18. P-ethyl-2-nitro-5-(2-fluoro-4-trifluoromethylphenoxy)phenylphosphinic chloride
19. P-ethyl-2-nitro-5-(4-chloro-2-nitrophenoxy)phenylphosphinic chloride
20. P-ethyl-2-nitro-5-(2-methoxy-4-methylphenoxy)phenylphosphinic chloride
21. P-ethyl-2-nitro-5-(2-bromo-4-chlorophenoxy)phenylphosphinic chloride
22. P-ethyl-2-nitro-5-(2-cyano-4-trifluoromethylphenoxy)phenylphosphinic chloride
23. P-ethyl-2-nitro-5-(2,6-dichloro-4-trifluoromethylphenoxy)phenylphosphinic chloride
24. P-methyl-2-nitro-5-(2-chloro-4-trifluoromethylphenoxy)phenylphosphinic chloride
25. P-methyl-2-nitro-5-(2-fluoro-4-trifluoromethylphenoxy)phenylphosphinic chloride 26. P-n-propyl-2-nitro-5-(2-chloro-4-trifluoromethylphenoxy)phenylphosphinic chloride
27. P-phenyl-2-nitro-5-(2-chloro-4-trifluoromethylphenoxy)phenylphosphinic chloride

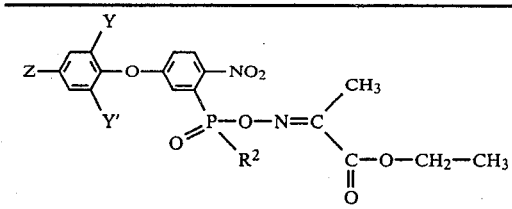

IV

| | Y | Y' | Z | R² |
|---|---|---|---|---|
| 16. | H | H | CF₃ | CH₂CH₃ |
| 17. | H | H | Cl | CH₂CH₃ |
| 18. | F | H | CF₃ | CH₂CH₃ |
| 19. | NO₂ | H | Cl | CH₂CH₃ |
| 20. | OCH₃ | H | CH₃ | CH₂CH₃ |
| 21. | Br | H | Cl | CH₂CH₃ |
| 22. | C≡N | H | CF₃ | CH₂CH₃ |
| 23. | Cl | Cl | CF₃ | CH₂CH₃ |
| 24. | Cl | H | CF₃ | CH₃ |
| 25. | F | H | CF₃ | CH₃ |
| 26. | Cl | H | CH₃ | CH₂CH₂CH₃ |
| 27. | Cl | H | CF₃ | C₆H₅ |

EXAMPLE 6

Following the procedure of Example 1, dimethyl ethylphosphonite is reacted with each of 4-(2-chloro-4-trifluoromethylphenylthio)-1,2-dinitrobenzene, 4-(2-chloro-4-trifluoromethylanilino)-1,2-dinitrobenzene and 4-(2-chloro-4-trifluoromethylbenzyl)-1,2-dinitrobenzene to yield, respectively, methyl P-ethyl-2-nitro-5-(2-chloro-4-trifluoromethylphenylthio)phenylphosphinate, methyl P-ethyl-2-nitro-5-(2-chloro-4-trifluoromethylanilino)phenylphosphinate, and methyl P-ethyl-2-nitro-5-(2-chloro-4-trifluoromethylbenzyl)phenylphosphinate.

Each of the above phosphinates is halogenated, following Example 2 procedures, to the corresponding phosphinic chloride. Each of the phosphinic chlorides is reacted with ethyl 2-hydroxyiminopropionate to yield, respectively,
ethyl 2-[P-ethyl-2-nitro-5-(2-chloro-4-trifluoromethylphenylthio)phenylphosphenyloxyimino]propionate,
ethyl 2-[P-ethyl-2-nitro-5-(2-chloro-4-trifluoromethylanilino)phenylphosphinyloxyimino]propionate, and
ethyl 2-[P-ethyl-2-nitro-5-(2-chloro-4-trifluoromethylbenzyl)phenylphosphinyloxyimino]propionate.

EXAMPLE 7

A solution of methyl P-ethyl-2-nitro-5-(2-chloro-4-trifluoromethylphenoxy)phenylphosphinate (5.5 mmol) in methanol (10 ml) is hydrogenated with 10% Pd/C (200 mg) at 1 atmosphere for 30 min. to give, after filtration and evaporation, methyl P-ethyl-2-amino-5-(2-chloro-4-trifluoromethylphenoxy)phenylphosphinate.

The amino phosphinate is diazotized following the procedure described in Org. Synth. Coll. Vol. 1:514 (1932). The resulting diazo salt is treated with, respectively, cuprous cyanide (1.2 eq.) or cuprous chloride (1.2 eq.) in benzene-water solution. When each reaction is completed, the organic phase is separated, washed, dried and purified by TLC to yield, respectively, methyl P-ethyl-2-cyano-5-(2-chloro-4-trifluoromethylphenoxy)phenylphosphinate or methyl P-ethyl-2-chloro-5-(2-chloro-4-trifluoromethylphenoxy)phenylphosphinate.

Each of methyl P-ethyl-2-amino-5-(2-chloro-4-trifluoromethylphenoxy)phenylphosphinate, methyl P-ethyl-2-cyano-5-(2-chloro-4-trifluoromethylphenoxy)phenylphosphinate, and methyl P-ethyl-2-chloro-5-(2-chloro-4-trifluoromethylphenoxy)phenylphosphinate is hydrolyzed to the corresponding acid and then halogenated, following Example 1 procedures, or is directly halogenated, following Example 2 procedures, to give, respectively, P-ethyl-2-amino-5-(2-chloro-4-trifluoromethylphenoxy)phenylphosphinic chloride, P-ethyl-2-cyano-5-(2-chloro-4-trifluoromethylphenoxy)phenylphosphinic chloride, and P-ethyl-2-chloro-5-(2-chloro-4-trifluoromethylphenoxy)phenylphosphinic chloride. Each of these phosphinic chlorides is reacted with ethyl 2-hydroxyiminopropionate to yield, respectively,
ethyl 2-[P-ethyl-2-amino-5-(2-chloro-4-trifluoromethylphenoxy)phenylphosphinyloxyimino]propionate,
ethyl 2-[P-ethyl-2-cyano-5-(2-chloro-4-trifluoromethylphenoxy)phenylphosphinyloxyimino]propionate, and
ethyl 2-[P-ethyl-2-chloro-5-(2-chloro-4-trifluoromethylphenoxy)phenylphosphinyloxyimino]propionate.

EXAMPLE 8

Following the procedure of Example 1 or 2, P-ethyl-2-nitro-5-(3-chloro-5-trifluoromethyl-2-pyridyloxy)phenylphosphinate is reacted with each of the hydroxyimino compounds under column V to prepare the corresponding phosphinyloxyimino compound under column VII.

V 28. ethyl 2-hydroxyiminopropionate
29. methyl 2-hydroxyimino-3-methylbutanoate
30. methyl 2-hydroxyimino-2-phenylacetate
31. 3-hydroxyimino-2-butanone
32. 2-hydroxyiminopropanoic acid
33. 2-hydroxyiminopropiophenone
34. 4-hydroxyimino-4-(4-chlorophenyl)-3-butanone
35. 2-hydroxyimino-3-methylbutanoic acid
36. 4'-chloro-2-hydroxyiminobutyrophenone
37. 4-hydroxyimino-3-butanone
38. methyl 2-hydroxyiminoacetate
39. methyl 2-hydroxyiminopropionate
40. ethyl 2-hydroxyiminopropionthioate In the same manner, each of the phophinic chlorides under column VI is reacted with ethyl 2-hydroxyiminopropionate to give the corresponding phosphinyloxyimino compound under column VII.

VI

41. P-ethyl-2-nitro-5-(5-trifluoromethyl-2-pyridyloxy)phenylphosphinic chloride
42. P-ethyl-2-nitro-5-(5-chloro-2-pyridyloxy)phenylphosphinic chloride
43. P-ethyl-2-nitro-5-(3-fluoro-5-trifluoromethyl-2-pyridyloxy)phenylphosphinic chloride
44. P-ethyl-2-nitro-5-(5-chloro-3-nitro-2-pydridyloxy)phenylphosphinic chloride
45. P-ethyl-2-nitro-5-(3-methoxy-5-methyl-2-pyridyloxy)phenylphosphinic chloride
46. P-ethyl-2-nitro-5-(3-bromo-5-chloro-2-pyridyloxy)-phenylphosphinic chloride
47. P-ethyl-2-nitro-5-(3-cyano-5-trifluoromethyl-2-pyridyloxy)phenylphosphinic chloride 48. P-methyl-2-nitro-5-(3-chloro-5-trifluoromethyl-2-pyridyloxy)phenylphosphinic chloride
49. P-methyl-2-nitro-5-(3-fluoro-5-trifluoromethyl-2-pyridyloxy)phenylphosphinic chloride
50. P-n-propyl-2-nitro-5-(3-chloro-5-trifluoromethyl-2-pyridyloxy)phenylphosphinic chloride
51. P-phenyl-2-nitro-5-(3-chloro-5-trifluoromethyl-2-pyridyloxy)phenylphosphinic chloride

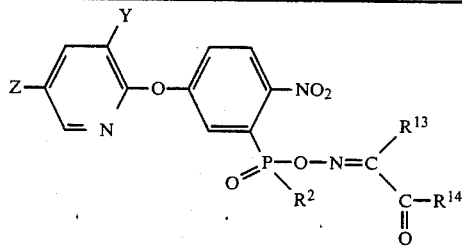

VII

| | Y | Z | $R^2$ | $R^{13}$ | $R^{14}$ |
|---|---|---|---|---|---|
| 28. | Cl | $CF_3$ | $CH_2CH_3$ | $CH_3$ | $OCH_2CH_3$ |
| 29. | Cl | $CF_3$ | $CH_2CH_3$ | $CH(CH_3)_2$ | $OCH_3$ |
| 30. | Cl | $CF_3$ | $CH_2CH_3$ | $C_6H_5$ | $OCH_3$ |
| 31. | Cl | $CF_3$ | $CH_2CH_3$ | $CH_3$ | $CH_3$ |
| 32. | Cl | $CF_3$ | $CH_2CH_3$ | $CH_3$ | OH |
| 33. | Cl | $CF_3$ | $CH_2CH_3$ | $CH_3$ | $C_6H_5$ |
| 34. | Cl | $CF_3$ | $CH_2CH_3$ | $(4\text{-Cl})C_6H_5$ | $CH_2CH_3$ |
| 35. | Cl | $CF_3$ | $CH_2CH_3$ | $CH(CH_3)_2$ | OH |
| 36. | Cl | $CF_3$ | $CH_2CH_3$ | $CH_2CH_3$ | $(4\text{-Cl})C_6H_5$ |
| 37. | Cl | $CF_3$ | $CH_2CH_3$ | H | $CH_2CH_3$ |
| 38. | Cl | $CF_3$ | $CH_2CH_3$ | H | $OCH_3$ |
| 39. | Cl | $CF_3$ | $CH_2CH_3$ | $CH_3$ | $OCH_3$ |
| 40. | Cl | $CF_3$ | $CH_2CH_3$ | $CH_3$ | $SCH_2CH_3$ |
| 41. | H | $CF_3$ | $CH_2CH_3$ | $CH_3$ | $OCH_2CH_3$ |
| 42. | H | Cl | $CH_2CH_3$ | $CH_3$ | $OCH_2CH_3$ |
| 43. | F | $CF_3$ | $CH_2CH_3$ | $CH_3$ | $OCH_2CH_3$ |
| 44. | $NO_2$ | Cl | $CH_2CH_3$ | $CH_3$ | $OCH_2CH_3$ |
| 45. | $OCH_3$ | $CH_3$ | $CH_2CH_3$ | $CH_3$ | $OCH_2CH_3$ |
| 46. | Br | Cl | $CH_2CH_3$ | $CH_3$ | $OCH_2CH_3$ |
| 47. | C≡N | $CF_3$ | $CH_2CH_3$ | $CH_3$ | $OCH_2CH_3$ |
| 48. | Cl | $CF_3$ | $CH_3$ | $CH_3$ | $OCH_2CH_3$ |
| 49. | F | $CF_3$ | $CH_3$ | $CH_3$ | $OCH_2CH_3$ |
| 50. | Cl | $CF_3$ | $CH_2CH_2CH_3$ | $CH_3$ | $OCH_2CH_3$ |
| 51. | Cl | $CF_3$ | $C_6H_5$ | $CH_3$ | $OCH_2CH_3$ |

EXAMPLE 9

A mixture of methyl P-ethyl-2-nitro-5-(2-chloro-4-trifluoromethylphenoxy)phenylphosphinate (4.7 mmol) and phosphorus pentasulfide (1.2 mmol) is heated to 150°–160° under nitrogen for 3–4 hours. After cooling, the residue is purified by preparative thin-layer chromatography (on silica gel, eluting with 20% ethyl acetate/hexane) to give O-methyl P-ethyl-2-nitro-5-(2-chloro-4-trifluoromethylphenoxy)phenylphosphinothioate.

In like manner, O-methyl P-ethyl-2-nitro-5-(3-chloro-5-trifluoromethyl-2-pyridyloxy)phenylphosphinothioate is prepared from methyl P-ethyl-2-nitro-5-(3-chloro-5-trifluoromethyl-2-pyridyloxy)phenylphosphinate and phosphorus pentasulfide.

Each of the above two phosphinothioates is halogenated following the procedure of Example 2 to the corresponding phosphinothioic chlorides, each of which is then reacted with ethyl 2-hydroxyiminopropionate to yield, respectively, ethyl 2-[P-ethyl-2-nitro-5-(2-chloro-4-trifluoromethylphenoxy)phenylphosphinothiooxyimino]propionate, and ethyl 2-[P-ethyl-2-nitro-5-(3-chloro-5-trifluoromethyl-2-pyridyloxy)phenylphosphinothiooxyimino]propionate.

EXAMPLE 10

2-[P-ethyl-2-nitro-5-(2-chloro-4-trifluoromethylphenoxy)phenylphosphinyloxyimino]propionic acid (1 g) is combined with aqueous sodium hydroxide (1 eq.), with stirring at RT for about 2 hours. The reaction is then concentrated to dryness to yield the sodium salt of 2-[P-ethyl-2-nitro-5-(2-chloro-4-trifluoromethylphenoxy)phenylphosphinyloxyimino]propionic acid.

EXAMPLE 11

A mixture of 4-(2-chloro-4-trifluoromethylphenoxy)-1,2-dinitrobenzene (1.8 g, 4.97 mmol), sodium hypophosphite (0.88 g, 9.94 mmol) and cupric sulfate (180 mg) in 20 ml of methyl nitrile/water (4:1) is heated under reflux for 24 hours. The reaction is poured into water, extracted with methylene chloride, dried and chromatographed (silica gel, eluting with 10% methanol/chloroform) to yield 2-nitro-5-(2-chloro-4-trifluoromethylphenoxy)phenylphosphinic acid.

Following the procedure of Example 1, the phosphinic acid is halogenated to the corresponding phosphinic chloride, which is then reacted with ethyl 2-hydroxyiminopropionate to yield ethyl 2-[2-nitro-5-(2-chloro-4-trifluoromethylphenoxy)phenylphosphinyloxyimino]propionate.

EXAMPLE 12

Following the procedure of Example 1 or Example 2, P-ethyl-2-nitro-5-(2-chloro-4-trifluoromethylphenoxy)phenylphosphinic chloride is reacted with each of ethyl 2-hydroxyimino-2-(2-thienyl)acetate and methyl 2-hydroxyimino-2-(2-furyl)acetate to yield, respectively, ethyl 2-[P-ethyl-2-nitro-5-(2-chloro-4-trifluoromethylphenyloxy)phenylphosphinyloxyimino]-2-(2-thienyl)acetate, and methyl 2-[P-ethyl-2-nitro-5-(2-chloro-4-trifluoromethylphenoxy)phenylphosphinyloxyimino]-2-(2-furyl)acetate.

In the same way, P-ethyl-2-nitro-5-(2-chloro-4-trifluoromethylphenoxy)phenylphosphinic chloride is reacted with each of methyl 2-hydroxyimino-2-cyclohexylacetate and ethyl 2-hydroxyimino-2-cyclopropylacetate to yield, respectively, methyl 2-[P-ethyl-2-nitro-5-(2-chloro-4-trifluoromethylphenoxy)phenylphosphinyloxyimino]-2-cyclohexylacetate, and ethyl 2-[P-ethyl-2-nitro-5-(2-chloro-4-trifluoromethylphenoxy)phenylphosphinyloxyimino]-2-cyclopropylacetate.

EXAMPLE 13

To a solution of ethyl 2-[P-ethyl-2-nitro-5-(2-chloro-4-trifluoromethylphenoxy)phenylphosphinyloxyimino]propionate (500 mg) in tetrahydrofuran (10 ml) is added hydrazine (1 eq.) and 5% rhodium on activated charcoal (50 mg) at 15°–25°, with stirring for 2 hours. The reaction is then filtered and the filtrate is diluted with methylene chloride, washed, dried and concentrated to dryness to give ethyl 2-[P-ethyl-2-hydroxyamino-5-(2-chloro-4-trifluoromethylphenoxy)phenylphosphinyloxyimino]propionate.

A mixture of ethyl 2-[P-ethyl-2-hydroxyamino-5-(2-chloro-4-trifluoromethylphenoxy)phenylphosphinyloxyimino]propionate (400 mmol) and ferric chloride (600 mmol) in aqueous ethanol (1:3 water:ethanol; 10 ml) is stirred at RT for 10 min. The reaction is filtered and the filtrate is diluted with methylene chloride, washed, dried and evaporated to dryness to give ethyl 2-[P-ethyl-2-nitroso-5-(2-chloro-4-trifluoromethylphenoxy)-phenylphosphinyloxyimino]propionate.

EXAMPLE 14

Post-emergence herbicidal activity on the grasses green foxtail, watergrass, shattercane and wild oats and on the broadleafs annual morningglory, mustard, soybean and velvetleaf was tested for the compound ethyl 2-[P-ethyl-2-nitro-5-(2-chloro-4-trifluoromethylphenoxy)phenylphosphinyloxyimino]propionate by spraying seedlings with a solution of water/acetone (1:1), surfactant (1%) and test compound at a rate equivalent to 10 lb/acre. The average activity, in percent control, is 88% on grasses and 100% on broadleafs.

Pre-emergence herbicidal activity of ethyl 2-[P-ethyl-2-nitro-5-(2-chloro-4-trifluoromethylphenoxy)phenylphosphinyloxyimino]propionate was tested on the above grasses and broadleafs (but with nightshade substituted for soybean) at a rate equivalent to 10 lb/acre. The average activity, in percent control, is 99% on grasses and 100% on broadleafs.

What is claimed is:

1. A compound of the formula:

(A)

wherein,

R is the group

W is oxygen or sulfur;
X is oxygen, sulfur, amino or methylene;
Y is hydrogen, lower alkyl, lower alkoxy, lower haloalkyl, lower haloalkoxy, halogen, cyano or nitro;
Z is independently selected from the values of Y; t is zero, one or two:
$R^2$ is hydrogen, lower alkyl or phenyl;
$R^3$ is cyano, nitro, nitroso, amino, hydroxyamino or chloro:
$R^{13}$ is hydrogen, lower alkyl, lower cycloalkyl, phenyl, substituted phenyl, furyl or thienyl; and
$R^{14}$ is OH, $O^-Na^+$, lower alkyl, lower alkoxy, lower alkylthio, phenyl, substituted phenyl, phenoxy, phenylthio or benzyloxy.

2. A compound of the following formula, according to claim 1:

3. A compound according to claim 2 wherein $R^2$ is methyl or ethyl; $R^3$ is cyano or nitro; and W is oxygen.

4. A compound according to claim 3 wherein t is zero or one, Y is chloro or fluoro and Z is chloro or trifluoromethyl.

5. A compound according to claim 4 wherein $R^{13}$ is methyl, ethyl, isopropyl or phenyl; and $R^{14}$ is methyl, ethyl, methoxy, ethoxy or phenyl.

6. A compound according to claim 5 wherein $R^2$ is ethyl, $R^3$ is nitro and $R^{14}$ is methoxy or ethoxy.

7. The compound ethyl 2-[P-ethyl-2-nitro-5-(2-chloro-4-trifluoromethylphenoxy)phenylphosphinyloxyimino]propionate, according to claim 6.

8. The compound methyl 2-[P-ethyl-2-nitro-5-(2-chloro-4-trifluoromethylphenoxy)phenylphosphinyloxyimino]-3-methylbutanoate, according to claim 6.

9. A compound of the following formula, according to claim 1:

wherein, $R^2$ is methyl or ethyl; $R^3$ is cyano or nitro; W is oxygen; t is zero or one; Y is chloro or fluoro; and Z is chloro or trifluoromethyl.

10. A compound according to claim 9 wherein $R^{13}$ is methyl, ethyl, isopropyl or phenyl; and $R^{14}$ is methyl, ethyl, methoxy, ethoxy or phenyl.

11. A method for the control of weeds which comprises treating said weed or its locus with a herbicidally effective amount of a compound of formula (A) as defined in claim 1.

12. A composition for the control of weeds which comprises a herbicidally effective amount of a compound of formula (A) as defined in claim 1 and a suitable liquid or solid carrier.

* * * * *